US006958431B2

(12) United States Patent
Fields et al.

(10) Patent No.: US 6,958,431 B2
(45) Date of Patent: *Oct. 25, 2005

(54) DISTRIBUTION STRIP FOR ABSORBENT PRODUCTS

(75) Inventors: Sonja Fields, Memphis, TN (US); Howard Leon Schoggen, Southaven, MS (US); Jeffery Todd Cook, Germantown, TN (US); Judson Fidler, Cordova, TN (US)

(73) Assignee: BKI Holding Corporation, Wilmington, DE (US)

( * ) Notice: Subject to any disclaimer, the term of this patent is extended or adjusted under 35 U.S.C. 154(b) by 5 days.

This patent is subject to a terminal disclaimer.

(21) Appl. No.: 10/603,440

(22) Filed: Jun. 24, 2003

(65) Prior Publication Data

US 2004/0006322 A1 Jan. 8, 2004

Related U.S. Application Data

(63) Continuation of application No. 10/137,832, filed on May 1, 2002, now Pat. No. 6,649,809, which is a continuation of application No. 09/593,409, filed on Jun. 14, 2000, now Pat. No. 6,495,734.
(60) Provisional application No. 60/139,163, filed on Jun. 14, 1999.

(51) Int. Cl.[7] .................................................. A61F 13/15
(52) U.S. Cl. ....................... 604/375; 604/374; 604/378; 604/377
(58) Field of Search ................................. 604/380, 367, 604/368, 374, 375, 378, 384, 385.101, 385.23, 386, 387

(56) References Cited

U.S. PATENT DOCUMENTS

| 4,798,603 | A |   | 1/1989  | Meyer et al.             |
|-----------|---|---|---------|--------------------------|
| 4,888,231 | A |   | 12/1989 | Angstadt                 |
| 4,898,642 | A | * | 2/1990  | Moore et al. ... 162/157.6 |
| 5,492,759 | A |   | 2/1996  | Eriksson et al.          |
| 5,531,728 | A |   | 7/1996  | Lash                     |
| 5,549,589 | A | * | 8/1996  | Horney et al. ...... 604/366 |
| 5,562,645 | A |   | 10/1996 | Tanzer et al.            |
| 5,593,399 | A |   | 1/1997  | Tanzer et al.            |
| 5,601,921 | A |   | 2/1997  | Eriksson                 |
| 5,607,414 | A |   | 3/1997  | Richards et al.          |
| 5,669,895 | A |   | 9/1997  | Murakami et al.          |
| 5,855,572 | A |   | 1/1999  | Schmidt                  |
| 5,895,379 | A |   | 4/1999  | Litchholt et al.         |
| 6,037,518 | A |   | 3/2000  | Guidotti et al.          |

FOREIGN PATENT DOCUMENTS

| EP | 0 631 768 A1   | 1/1995 |
| EP | 0 512 010 B1   | 9/1997 |
| WO | WO 92/11830    | 7/1992 |
| WO | WO-95/17869 A1 | 7/1995 |

* cited by examiner

Primary Examiner—Jacqueline F. Stephens
(74) Attorney, Agent, or Firm—Darby & Darby

(57) ABSTRACT

Disclosed are absorbent structures for use in disposable absorbent products for absorbing bodily fluids, wherein the absorbent structure includes a fluid storage layer including matrix fibers and a superabsorbent polymer for receiving fluids and a distribution strip positioned below the fluid storage layer. The distribution strip includes cellulosic fibers and has a basis weight of between 45 grams per square meter and 140 grams per square meter and a density of between 0.20 grams per cubic centimeter and 0.60 grams per cubic centimeter.

6 Claims, 3 Drawing Sheets

DISTRIBUTION STRIP FOR ABSORBENT PRODUCTS

This is a continuation of application Ser. No. 10/137,832, filed May 1, 2002 now U.S. Pat. No. 6,649,809 which is a continuation of Ser. No. 09/593,409 now U.S. Pat. No. 6,495,734, filed Jun. 14, 2000 which claims benefit of application Ser. No. 60/139,163, filed Jun. 14, 1999. Each of these prior applications is hereby incorporated herein by reference, in its entirety.

FIELD OF THE INVENTION

The present invention relates to an absorbent structure including chemically treated and mercerized cellulose fibers for improved liquid distribution for use in disposable absorbent structures such as infant diapers, feminine hygiene pads and adult incontinence pads.

BACKGROUND OF THE INVENTION

Absorbent products, such as infant diapers, feminine hygiene pads, adult incontinence pads, and the like, have traditionally utilized structures with various configurations and materials to provide the requisite absorbency performance. One objective in developing improved absorbent products has been to increase both the total absorbent capacity of the product, as well as the tenacity and reliability with which such products absorb and retain fluid loads. Another objective has been to provide thinner and more comfortable absorbent products.

To manage liquid body waste, the absorbent structure or structures within an absorbent product must generally be able to first uptake a liquid into the absorbent product, then distribute the liquid within the absorbent product, and finally retain the liquid within the a One way for improving the absorbency characteristics of an absorbent product has been to use entangled masses of fibers, e.g., non-woven fibrous webs, which can imbibe and retain liquids, such as discharged body fluids and other body exudates, both by absorption (e.g., fluid is taken up by the fiber material itself and retained in the capillary interstices between the fiber) and by wicking (e.g., fluid is distributed through diffusion and stored in the capillary interstices between fibers). Typically, however, structures of this type have had a limited storage capacity for fluids, a low rate of distributing fluids, and a limited ability to partition fluids from other materials.

Conventional fluff cellulose fibers and superabsorbent polymers are widely used for the absorbent core of absorbent products. Superabsorbent polymers (hereinafter "SAPs") are capable of absorbing many times their own weight of liquid. SAPs have been used to increase the absorbency of absorbent products such as infant diapers, feminine hygiene pads and adult incontinence pads.

While an absorbent core of fiber and SAPs can provide improved storage characteristics, they can have shortcomings in transporting or distributing absorbed body fluids laterally from one region or zone to another. This can be troublesome in some products where body fluids are frequently discharged in periodic discrete gushes, and each gush of fluid discharged in this manner will generally encounter an absorbent structure with diminished capabilities to quickly and efficiently: (1) acquire subsequent gushes of fluid, (2) move fluid from the common discharge area to other unused, unsaturated, or relatively dry parts of the absorbent structure, (3) remain resistant to compression deflection, (4) recover from wet compression, and (5) partition fluids. Thus, the total absorbent capacity of the absorbent product is often not fully utilized.

It is an object of the present invention to provide an absorbent article able to exceed the wicking, partitioning or distribution characteristics of known absorbent structures.

Furthermore, it is an object of the present invention to have an absorbent structure that is capable of quickly distributing the liquid throughout the absorbent product.

SUMMARY OF THE INVENTION

The present invention is directed to an absorbent structure for use in a disposable absorbent product for absorbing bodily fluids. The absorbent structure includes a fluid storage layer including matrix fibers and a superabsorbent polymer for receiving fluids and a distribution strip positioned below said fluid storage layer. The distribution strip including cellulosic fibers and has a basis weight of between 45 grams per square meter and 140 grams per square meter and has a density of between 0.20 grams per cubic centimeter and 0.60 grams per cubic centimeter.

DETAILED DESCRIPTION OF THE INVENTION

The present invention concerns a distribution strip useful for laterally wicking fluid. The distribution strip is particularly suitable as a component of a disposable absorbent product, such as a diaper. In such a product the distribution strip is ideally positioned beneath an absorbent storage component of the absorbent product.

The distribution strip is provided as a fibrous web. As used herein, the term "fiber" or "fibrous" is meant to refer to a particular material wherein the length to diameter ratio of such particulate material is greater than about 10. Conversely, a "nonfiber" or "nonfibrous" material is meant to refer to a particulate material wherein the length to diameter ratio of such particulate material is about 10 or less.

The fibers used in manufacturing the distribution strip may be chemically treated or mercerized. Preferred fibers include cellulosic fluff pulp, mercerized cellulose pulp, cotton linters and cellulose fluff pulp treated with polyvalent metal ions (e.g., aluminum, calcium or magnesium). Mixtures of these fibers may also be employed.

The distribution strip may be manufactured from individual fibers by either wetlaid or airlaid processes, although wetlaid processing is preferred. Additives typically used in wetlaid processes, such as wet strength resins (e.g., polyamide epichlorohydrin) may also be included.

Alternatively, the distribution strip may be made by an airlaid process, either as a separate web, or laid down as an integral layer with the other layers of the structure.

The basis weight of the distribution strip is preferably between 45 grams per square meter (gsm) and 140 gsm, and most preferably between 75 gsm and 110 gsm. The density of the distribution strip is preferably between 0.20 grams per cubic centimeter (g/cc) and 0.60 g/cc and most preferably between 0.25 g/cc and 0.55 g/cc.

Figure 1:
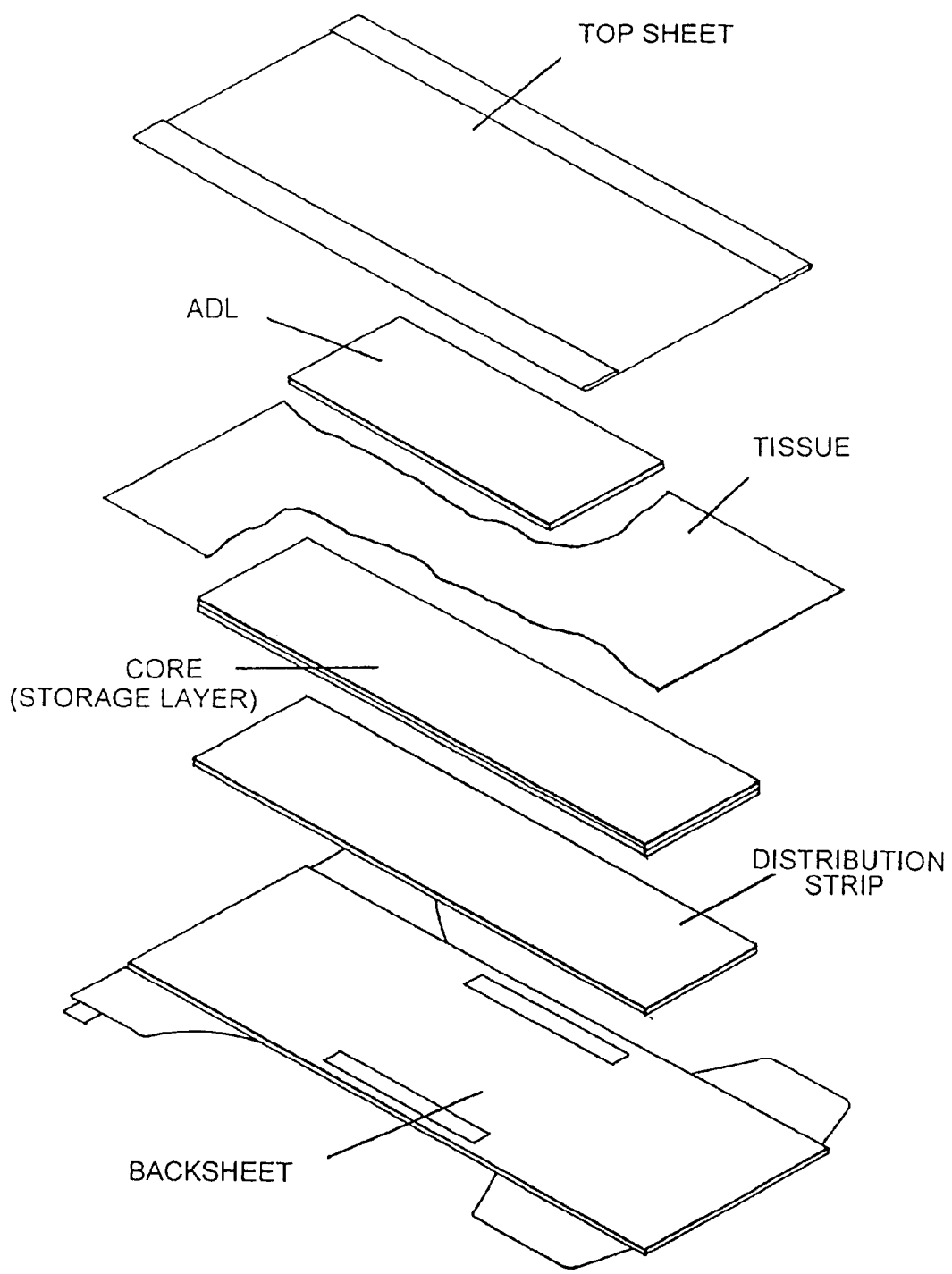
FIG. 1 is an exploded, perspective view of the components of an absorbent product with the distribution strip of the present invention.

In use, the distribution strip may be positioned in an absorbent structure in any orientation for which lateral (or X-Y) wicking of absorbed fluid is desired. For example, the absorbent structure in a conventional disposable diaper, as shown for example in FIG. 1, includes in order, a fluid permeable topsheet, a fluid acquisition and distribution layer (ADL), a fluid storage layer (typically including SAP particles) and a fluid impermeable bottom sheet. A fluid insult introduced to the diaper (in the Z-direction) penetrates the topsheet and is readily absorbed by the acquisition and distribution layer. The fluid is then distributed by the ADL which is designed to allow the liquid to wick laterally (in the X-Y direction). Finally fluid migrates from the ADL into the storage layer where it is absorbed by the fiber matrix and SAP particles.

Although a conventional diaper design as described above generally works well, one disadvantage is that in use, absorbed fluid tends to pool in one lateral region of the diaper (generally the front of the diaper). It would be desirable to provide a diaper which more efficiently wicks fluid from one portion of the diaper (e.g., the front) to another (e.g., the back) portion of the diaper which is generally under utilized.

The distribution strip of the present invention may be positioned between the fluid storage layer and the fluid-impermeable bottom sheet. In use, excess fluid collecting between the storage layer and the bottom sheet migrates into the distribution strip. The fluid then migrates laterally along the distribution strip to another region of the storage layer which has not exceeded its storage capacity. The fluid then diffuses into the storage layer. In this way, the storage capacity of the diaper is more efficiently utilized.

The distribution strip of the present invention may be employed in any absorbent product where lateral wicking of fluid is desired. In addition to diapers, the distribution strip may be used in feminine hygiene products, and adult incontinence products.

EXAMPLE 1

A distribution strip according to the present invention was made as a wetlaid handsheet. Cellulose fluff pulp (Foley fluff pulp, Buckeye Technologies Inc., Memphis, Tenn.) was disintegrated in a TAPPI disintegrator (British Pulp Evaluation Apparatus, Mavis Engineering, Ltd., London, England). The fluff pulp was disintegrated for 600 counts (~5 minutes). While the raw material is disintegrating, the Dynamic Handsheet Former (Formette Dynamique, Centre Technique de L'industrie des Papiers Cartons & Celluloses) was readied for use.

A fine meshed forming screen is placed in the centrifuge basket of the handsheet former and smoothly molded to the sides of the basket. The spray arm is positioned within the centrifuge basket, being careful to ensure that the spray head does not come in contact with the bottom of the basket, and locked in place. The fiber slurry reservoir is filled with approximately 14 liters of water. The centrifuge basket is activated and brought up to speed, then water is added until the water fully covers the forming screen. At this point, the slurried fiber is taken from the disintegrator and added to the slurry reservoir, and the paddle agitator is activated in the reservoir.

The delivery system is readied by setting the flow valve and activating both the spray arm and the pump. The spray arm continues to cycle at 1200 rpm until the slurry reservoir has been emptied. Water is slowly drained from the centrifuge basket by opening the drain valve. An effort is made to prevent the centrifuge RPM's from dropping more than 10% during this process. Once all the water has been removed, the centrifuge is turned off and the brake is applied. When the basket stops, the spray arm is removed, and the formed sheet is split at the seam where the forming screen overlaps. The sheet and the screen are removed from the centrifuge basket and transferred to a single drum steam dryer with a 40" circumference. The formed sheet was 36" in length. Repetitive passes through the dryer may be required to bring the sheet to a fully dried condition. Sheets were made at a basis weight of 77.5 gsm and 108.5 gsm. Once dried, the sheet was densified by compression to a target density of 0.3 g/cc.

EXAMPLE 2

The experiment of Example 1 was repeated except that mercerized cellulose pulp (HPZ grade, obtained from Buckeye Technologies Inc., Memphis Tenn.) was substituted for the fluff pulp.

EXAMPLE 3

The experiment of Example 1 was repeated except that the cellulose pulp was previously treated with approximately 7000 ppm of $AlSO_4$, precipitated according to papermaking techniques.

EXAMPLE 4

The experiment of Example 1 was repeated except that cotton linter pulp (Grade 702, obtained from Buckeye Technologies Inc., Memphis Tenn.) was substituted for the fluff pulp.

EXAMPLE 4

Figure 2:
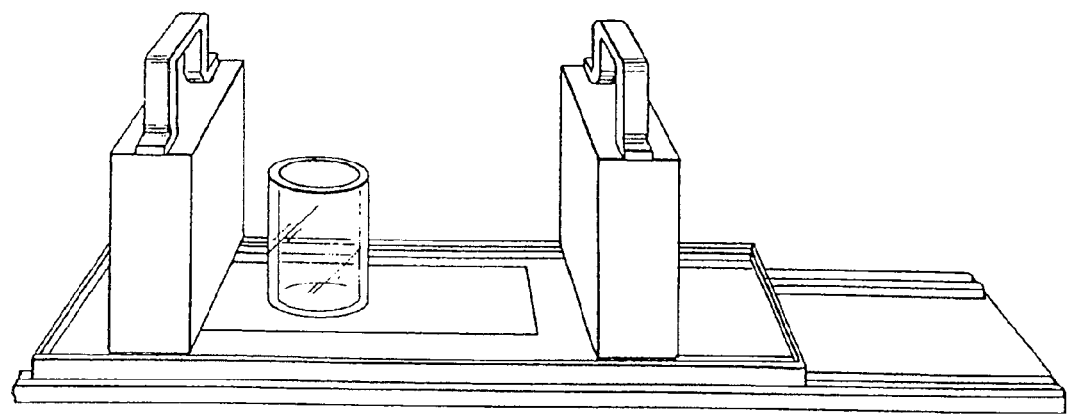
FIG. 2 is a perspective view of a horizontal wicking test apparatus employed in the Examples of the present specification.

The handsheets of Example 1–4 were subjected to horizontal wicking tests. A Kamas Cell Mill (Kamas Industri AB, Sweden) disintegrated Foley fluff pulp sheets to produce fluff for the absorbent core. A pad former (Buckeye Technologies Inc., Memphis, Tenn.) was used to combine SAP, SXM9100 (Stockhausen) and fluff in a 30% to 70% ratio in order to prepare 14"×14" absorbent core test pads. Test pads were constructed at a basis weight of 0.30 g/in$^2$ and compressed to a density of 0.15 g/cc. A distribution strip was cut to 4"×14" and conditioned in a controlled humidity and temperature room before testing. The distribution strips were constructed at a basis weight of 77.5 g/m$^2$ and compressed to a density of 0.30 g/cc. The samples were then placed onto a level platform with bordering grooves to capture "runoff" fluid (0.9% saline). (See FIG. 2 for wicking apparatus.) An acquisition-distribution layer (ADL) from a commercial diaper cut to 3"×7" was placed on top of the sample where fluid was introduced. A second board was placed on top of the sample and ADL. The top board contained an insult reservoir with a 1½ inside diameter. The insult region, relative to the sample, was 5" centered from the front end or end closest to insult reservoir. Two 4,539 g weights placed on the top board along with the weight of the top board supplied about 0.40 lbs/in² of pressure perpendicular to the sample. Three 100-ml insults were introduced to the sample at twenty-minute intervals. After one hour, the sample was then sectioned and weighed to determine the distance that liquid was transported away from the insult region. Horizontal wicking was quantified by the sum of the last three inches of wicking in the absorbent core on a gram of fluid per gram of SAP/fluff sample basis. Absorption capacity for SAP/fluff and ADL was recorded. Table 1 details the effect of incorporating the wicking strip into an absorbent product.

TABLE 1

| Components of Absorbent Core and Distribution Strip | Wicking Last three inches in the absorbent core (g/g) |
| --- | --- |
| Core - 50% SAP & 50% Fluff cellulose | 11 |
| Core - 70% SAP & 30% Fluff cellulose | 15 |
| Core - 70% SAP & 30% Fluff cellulose Distribution Strip - 100% Fluff cellulose | 22 |
| Core - 70% SAP & 30% Fluff cellulose Distribution Strip - 100% Mercerized cellulose | 26 |
| Core - 70% SAP & 30% Fluff cellulose Distribution Strip - Chemically treated cellulose | 22 |
| Core - 70% SAP & 30% Fluff Cellulose Distribution Strip - Cotton linters | 23 |

EXAMPLE 5

Rate of Advance Test

Figure 3:
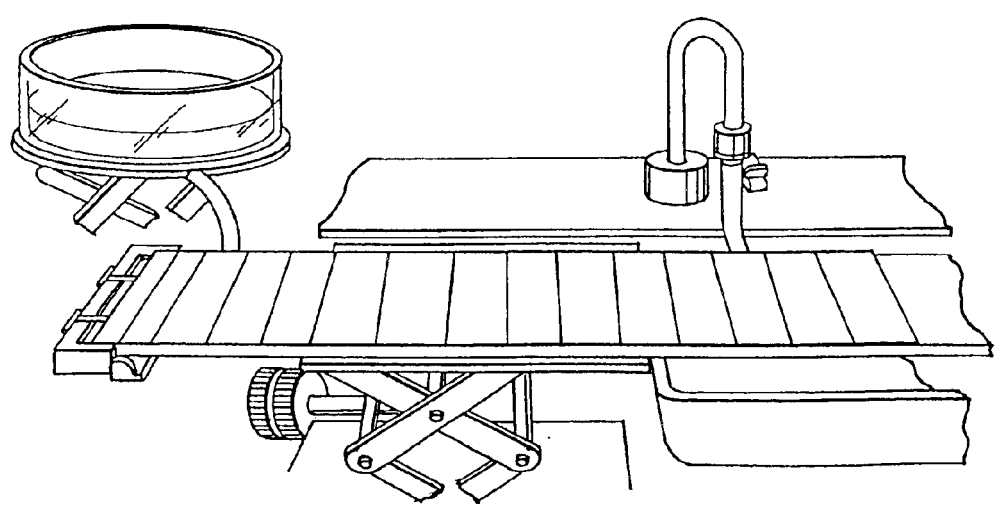
FIG. 3 is a perspective view of a rate of advance test apparatus employed in the Examples of the present specification.
Figure 4:
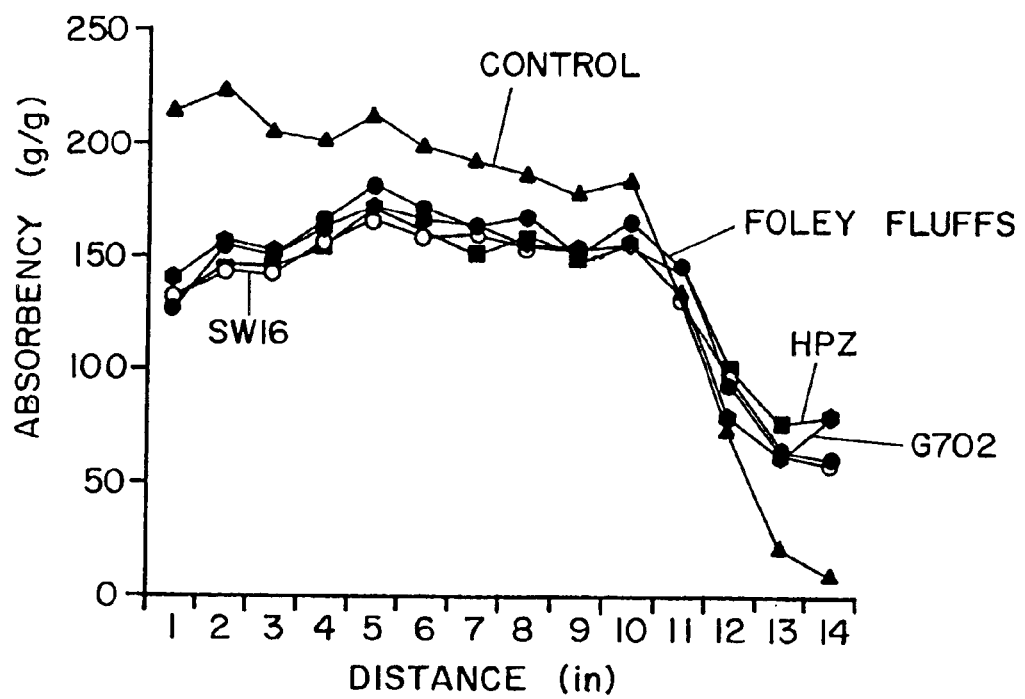
FIG. 4 is a graph illustrating the results of a horizontal wicking test performed on absorbent structures of the present invention.
Figure 5:
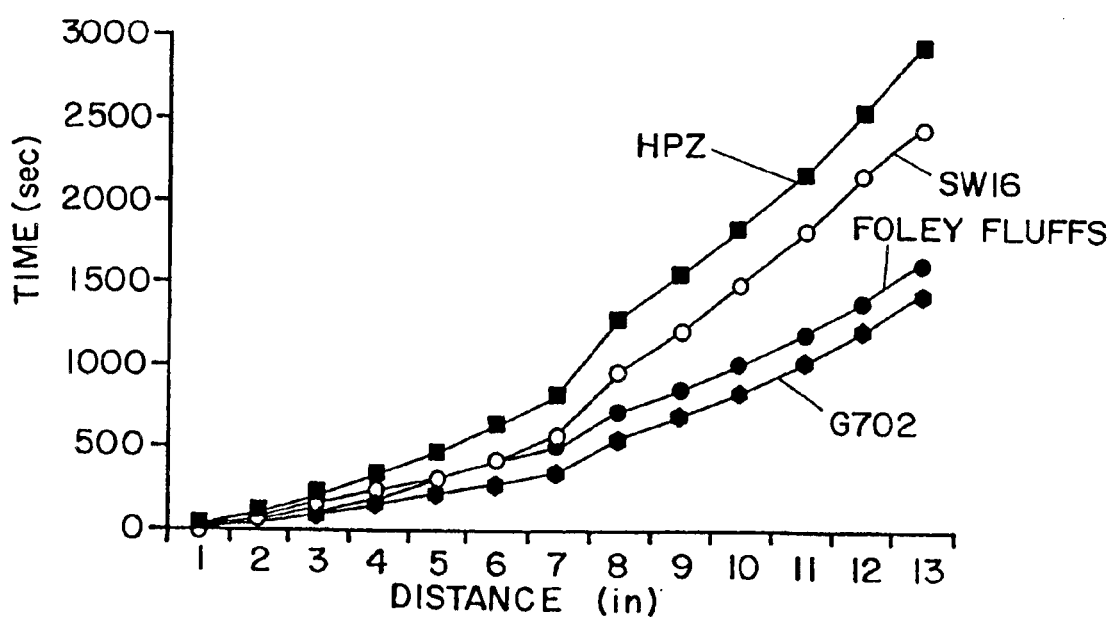
FIG. 5 is a graph illustrating the result of a rate of advance test performed on absorbent structures of the present invention.

Distribution strips were cut to 4"×14" and conditioned as above before testing. The distribution strips were constructed at a basis weight of 77.5 g/m² and compressed to a density of 0.30 g/cc. The samples were then placed onto a level platform with a Teflon coated mesh. A photograph of the testing apparatus is shown in FIG. 3. Attached to the platform was a fluid head box with ¼" tubing connected to a vertically adjustable fluid reservoir. The front edge of the distribution strip sample was centered above the head box. The head box was designed with four 3/16" diameter holes that were spaced 9/16" apart. The fluid (0.9% saline) level was adjusted to maintain zero head pressure. Once the sample touched the head box, fluid distributed along the sample. When the fluid reached the end of the sample the fluid reservoir was adjusted to prevent further fluid flow. Fluid distributed by the sample was measured as fluid rate in grams per second. Sample absorbency and fluid flow rate were recorded.

TABLE 2

| Distribution Strip Fiber | Fluid Rate g/sec | Absorbency g/g |
| --- | --- | --- |
| 100% Fluff cellulose | 0.11 | 7.5 |
| 100% Mercerized cellulose | 0.08 | 8.6 |
| 100% Chemically treated cellulose | 0.05 | 5.8 |
| 100% Cotton linters | 0.12 | 7.6 |

What is claimed is:

1. A distribution strip for use in an absorbent structure comprising cellulosic fibers selected from the group consisting of cotton linters, mercerized cellulose, chemically treated cellulose and mixtures thereof, wherein the chemically treated cellulose is treated with a polyvalent ion selected from the group consisting of aluminum, calcium, magnesium and mixtures thereof, and the distribution strip has a basis weight of between 45 grams per square meter and 140 grams per square meter and has a density of between 0.25 grams per cubic centimeter and 0.55 grams per cubic centimeter.

2. The distribution strip of claim 1, wherein the distribution strip has a basis weight of between 75 grams per square meter and 110 grams per square meter.

3. The distribution strip of claim 1, wherein the distribution strip is made by a wet-laid process.

4. The distribution strip of claim 1, wherein the distribution strip is made by an air-laid process.

5. The distribution strip of claim 1, wherein one hour after three 100 ml insults to the structure at 20 minute intervals in a last three inches of the fluid storage layer longitudinal and transverse horizontal wicking test, the fluid storage layer has horizontal wicking of 22 g/g or greater.

6. The distribution strip of claim 1, wherein the distribution strip has a fluid distribution rate of 0.05 grams per second or greater.

* * * * *